(12) United States Patent
Manning et al.

(10) Patent No.: US 11,090,031 B2
(45) Date of Patent: Aug. 17, 2021

(54) SYSTEMS, METHODS, AND APPARATUSES FOR THERMAL MANAGEMENT OF ULTRASOUND TRANSDUCERS

(71) Applicant: KONINKLIJKE PHILIPS N.V., Eindhoven (NL)

(72) Inventors: Ryan Manning, Reedsville, PA (US); Samuel Raymond Peters, Reedsville, PA (US); Gerred Price, Reedsville, PA (US)

(73) Assignee: KONINKLIJKE PHILIPS N.V., Eindhoven (NL)

(*) Notice: Subject to any disclaimer, the term of this patent is extended or adjusted under 35 U.S.C. 154(b) by 698 days.

(21) Appl. No.: 15/548,119

(22) PCT Filed: Jan. 22, 2016

(86) PCT No.: PCT/IB2016/050310
§ 371 (c)(1),
(2) Date: Aug. 2, 2017

(87) PCT Pub. No.: WO2016/125040
PCT Pub. Date: Aug. 11, 2016

(65) Prior Publication Data
US 2018/0263604 A1      Sep. 20, 2018

Related U.S. Application Data

(60) Provisional application No. 62/112,723, filed on Feb. 6, 2015.

(51) Int. Cl.
*A61B 8/00* (2006.01)

(52) U.S. Cl.
CPC ............ *A61B 8/546* (2013.01); *A61B 8/4444* (2013.01); *A61B 8/4483* (2013.01)

(58) Field of Classification Search
CPC ...... A61B 8/546; A61B 8/4444; A61B 8/4483
See application file for complete search history.

(56) References Cited

U.S. PATENT DOCUMENTS

| | | | |
|---|---|---|---|
| 5,545,942 A * | 8/1996 | Jaster | A61B 8/546 174/16.3 |
| 9,730,677 B2 * | 8/2017 | Davidsen | A61B 8/546 |
| 2005/0075573 A1 | 4/2005 | Park et al. | |
| 2006/0043839 A1 * | 3/2006 | Wildes | A61B 8/546 310/327 |
| 2007/0276248 A1 * | 11/2007 | Saito | A61B 8/546 600/459 |

(Continued)

FOREIGN PATENT DOCUMENTS

| | | |
|---|---|---|
| JP | 2001074710 A | 3/2011 |
| JP | 2014087556 A | 5/2014 |
| WO | 2014080312 A1 | 5/2014 |

*Primary Examiner* — Joanne M Hoffman

(57) ABSTRACT

Systems, methods, and apparatuses for dissipating heat from an ultrasound transducer are disclosed. A passive thermal management system including thermally conductive materials is disclosed. The passive thermal management system may include thermally conductive layers in a flexible circuit coupled to the transducer stack. The flexible circuit may be coupled to a thermally conductive bolster plate. The bolster plate may be coupled to a handle heat spreader that may be coupled to the interior surface of an ultrasound probe housing.

15 Claims, 5 Drawing Sheets

(56) References Cited

U.S. PATENT DOCUMENTS

| | | | |
|---|---|---|---|
| 2008/0009742 A1* | 1/2008 | Kondoh | G01N 29/2437 600/459 |
| 2009/0034370 A1* | 2/2009 | Guo | B06B 1/0622 367/180 |
| 2009/0062656 A1 | 3/2009 | Hyuga | |
| 2010/0125209 A1* | 5/2010 | Lee | B06B 1/0629 600/459 |
| 2010/0241004 A1* | 9/2010 | Jung | B06B 1/0622 600/459 |
| 2011/0062824 A1* | 3/2011 | Wada | B06B 1/0622 310/334 |
| 2012/0007471 A1* | 1/2012 | Tai | B06B 1/067 310/334 |
| 2012/0143060 A1* | 6/2012 | Weekamp | A61B 8/546 600/459 |
| 2012/0150038 A1* | 6/2012 | Osawa | G01S 7/5208 600/443 |
| 2013/0134834 A1* | 5/2013 | Yoshikawa | H01L 41/053 310/341 |
| 2013/0145611 A1 | 6/2013 | Guo | |
| 2013/0301395 A1* | 11/2013 | Hebrard | G01S 7/52079 367/189 |
| 2014/0375171 A1* | 12/2014 | Tai | B06B 1/0622 310/341 |
| 2015/0011889 A1* | 1/2015 | Lee | A61B 8/4444 600/459 |
| 2015/0289851 A1 | 10/2015 | Kobayashi et al. | |
| 2017/0164926 A1* | 6/2017 | Spicci | A61B 8/4281 |

* cited by examiner

SYSTEMS, METHODS, AND APPARATUSES FOR THERMAL MANAGEMENT OF ULTRASOUND TRANSDUCERS

This application is the U.S. National Phase application under 35 U.S.C. § 371 of International Application No. PCT/IB2016/050310, filed on Jan. 22, 2016, which claims the benefit of Provisional Application Ser. No. 62/112,723, filed Feb. 6, 2015. These applications are hereby incorporated by reference herein.

BACKGROUND

Ultrasound transducer arrays produce ultrasound waves for a variety of applications such as imaging, cleaning, and therapeutic treatment of tissue. Many ultrasound transducers convert electrical energy into ultrasound waves, and heat may be produced as a byproduct of the conversion. The heat may require dissipation to avoid damaging the transducer and/or a surface with which the ultrasound transducer is in contact. For example, a medical ultrasound transducer may burn the skin of a patient if heat produced by the transducer is not dissipated adequately.

Ultrasound transducers may have active and/or passively thermal management systems. Passive systems may include materials that draw heat away from the transducer. For example, an ultrasound probe may include a backing material below the transducer that may dissipate heat away from the transducer surface. However, current passive thermal management systems may not be adequate for new, higher power ultrasound applications such as shear wave imaging. Active thermal management systems may include, for example, circulating liquid coolants and/or spinning fans adjacent to the transducer array. While active thermal management systems may be capable of dissipating more heat than passive systems, active systems may increase the size, cost, and power consumption of the ultrasound system.

SUMMARY

An example ultrasound probe according to an embodiment of the disclosure may include a transducer stack, a backing block including a first surface, a second surface opposite the first surface, and a side extending between the first and second surfaces, and a flexible circuit, the flexible circuit may include: a central portion disposed between the transducer stack and the backing block, a wing portion coupled to the central portion, the wing portion may be configured to fold adjacent to the side of the backing block, a first heat cover disposed below the central portion and adjacent to the first surface of the backing block wherein the first heat cover may be configured to dissipate heat from the transducer stack, and a second heat cover disposed over the wing portion, wherein the second heat cover may be configured to dissipate heat from the transducer stack. The ultrasound probe may further include a bolster plate in thermal contact with the second heat cover, and a handle heat spreader in thermal contact with the bolster plate, wherein the handle heat spreader may be configured to dissipate heat from the bolster plate.

An example thermal management system according to an embodiment of the disclosure may include a top heat cover that may be configured to be applied to an upper surface of a flexible circuit, wherein the top heat cover may be configured to dissipate heat from a transducer stack, a bolster plate in thermal contact with the top heat cover, and a handle heat spreader in thermal contact with the bolster plate, wherein the handle heat spreader may be configured to dissipate heat from the bolster plate, the handle heat spreader further may be configured to conform to an interior surface of a probe housing, the probe housing may be configured to at least partially enclose the thermal management system.

An example ultrasound probe according to an embodiment of the disclosure may include a transducer stack, and a flexible circuit, including: a central portion disposed below the transducer stack, wing portions extending from parallel sides of the central portion, a first heat cover on the central portion, wherein the first heat cover may be configured to dissipate heat from the transducer stack, a first non-conductive layer on the wing portions, the first non-conductive layer coupled to two parallel sides of the first heat cover, a second non-conductive layer over the first heat cover, a first conductive trace layer over the first and second non-conductive layers, a non-conductive substrate over the first conductive trace layer, a second conductive trace layer over the first non-conductive substrate, a non-conductive top cover over the second conductive trace layer on the wing portions, and a second heat cover over at least a portion of the non-conductive top cover, wherein the second heat cover may be configured to dissipate heat from the first heat cover. The ultrasound probe may further include a handle heat spreader in thermal contact with the second heat cover, wherein the handle heat spreader may be configured to dissipate heat from the second heat cover.

DETAILED DESCRIPTION

Figure 1:
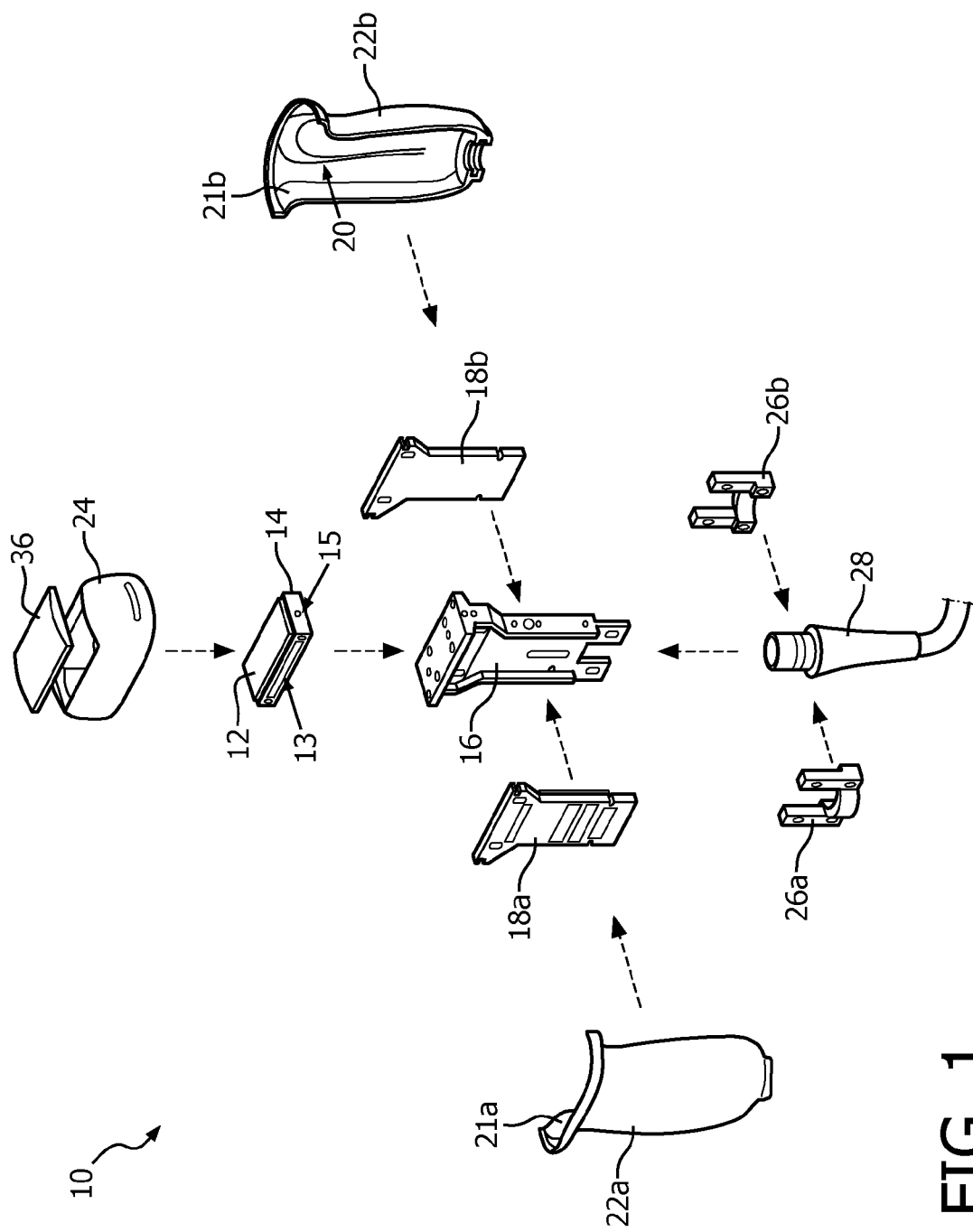
FIG. 1 is a schematic illustration of an exploded view of an ultrasound probe according to an embodiment of the disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

An ultrasound probe may be used for imaging, medical therapy, or other applications. The ultrasound probe includes an ultrasound transducer to produce and receive ultrasound signals (e.g., waves, pulses, sequences). The transducer may generate heat as it produces and/or receives ultrasound signals. If the temperature of the transducer increases above a threshold temperature, the transducer and/or an object in contact with the transducer may be damaged.

To manage the increase in temperature of the transducer, the probe may include components to passively dissipate the heat generated by the transducer. The components may include thermally conductive materials in thermal contact with the transducer and may dissipate heat from the transducer through multiple thermal paths. The components may be coupled to one another and/or positioned parallel relative to each other in the probe. Some of the components may be layers and/or films of thermally conductive materials that may dissipate heat without requiring an increase in probe size and/or increasing the weight of the probe such that it becomes difficult for a user to manipulate. The components may dissipate the heat over a wide area. This may prevent the occurrence of "hot spots," that is, localized sections of the ultrasound probe that have a greater temperature than the surrounding probe. Hot spots may damage other portions of the ultrasound probe and/or make the ultrasound probe uncomfortable or dangerous to handle by a user. The components for dissipating heat from the transducer may be referred to generally as a thermal management system.

FIG. 1 is a schematic illustration of an exploded view of an ultrasound probe 10 according to an embodiment of the disclosure. The ultrasound probe 10 may include a housing 22 which may form the handle portion of the probe that is held by a sonographer during use. The distal end of the probe 10 may be enclosed by a nosepiece housing 24. Behind a lens 36 covering the distal end is a transducer stack 12. The transducer stack 12 may be a matrix array transducer or another transducer type. The transducer stack 12 may include a flexible circuit and portions of a thermal management system (not shown in FIG. 1). Behind the transducer stack 12 may be a backing block 14 which may attenuate acoustic reverberations from the back of the transducer array and may conduct heat developed in the transducer stack 12 away from the distal end of the probe. The backing block 14 may include graphite in some embodiments. The backing block 14 may include two parallel sides 13 and two parallel sides 15. The sides 13 and sides 15 may be perpendicular to each other. In some embodiments, the sides 13 and sides 15 may be the same length.

A probe frame 16 may be in thermal contact with the back of the backing block 14 and may conduct heat further away from the distal end of the probe 10. The probe frame 16 may be implemented using aluminum, magnesium, steel, and/or a combination of materials. The frame 16 may be used as a mount for electrical components of the probe 10. For example, the electrical components may be mounted on printed circuit boards (PCB) 18a-b, which may be mounted to the frame 16. Although FIG. 1 shows two PCB's 18a-b, one PCB or more than two PCB's may be included in some embodiments. The PCBs 18a-b may be coupled to the flexible circuit of the transducer stack 12.

At the back of the probe 10 and extending from the proximal end of the probe 10 may be a cable 28. In some embodiments, the cable 28 may be clamped to the rear of the frame 16 by a clamp 26a-b. Other attachment methods may also be used. The cable 28 may couple the probe 10 to an ultrasound imaging system (not shown). In some embodiments, the cable 28 may include a metal braid (not shown), which may be in thermal contact with the frame 16. The metal braid may conduct heat from the frame 16 along the cable 28. The frame 16, circuit boards 18a-b, and/or other internal components of the probe 10 may be enclosed in the housing 22. The housing 22 may include two separate portions 22a-b that may be configured to fit together with each other and with the nose housing 24 to form an impervious housing to protect the ultrasound components from electromagnetic field interference, liquids, and/or debris. The housing 22 may comprise plastic, metal, rubber, and/or a combination of materials. In some embodiments, the nose housing 24 may be omitted, and the housing 22 may be configured to enclose the transducer stack 12 and backing block 14.

The housing 22 may include a handle heat spreader 20 on the interior surface 21a-b of each portion of the housing 22a-b (Only one handle heat spreader 20 is visible in FIG. 1). The handle heat spreader 20 may be a component of a probe thermal management system. The handle heat spreader 20 may include a copper layer. Other metals and/or thermally conducting materials may also be used. The handle heat spreader 20 may be coupled to the housing 22 by an adhesive or another attachment method may be used. The handle heat spreader 20 may conform to the interior surface 21a-b of the housing 22a-b. The handle heat spreader 20 may be coupled to one or more other components of the thermal management system included in the transducer stack 12.

Figure 2:
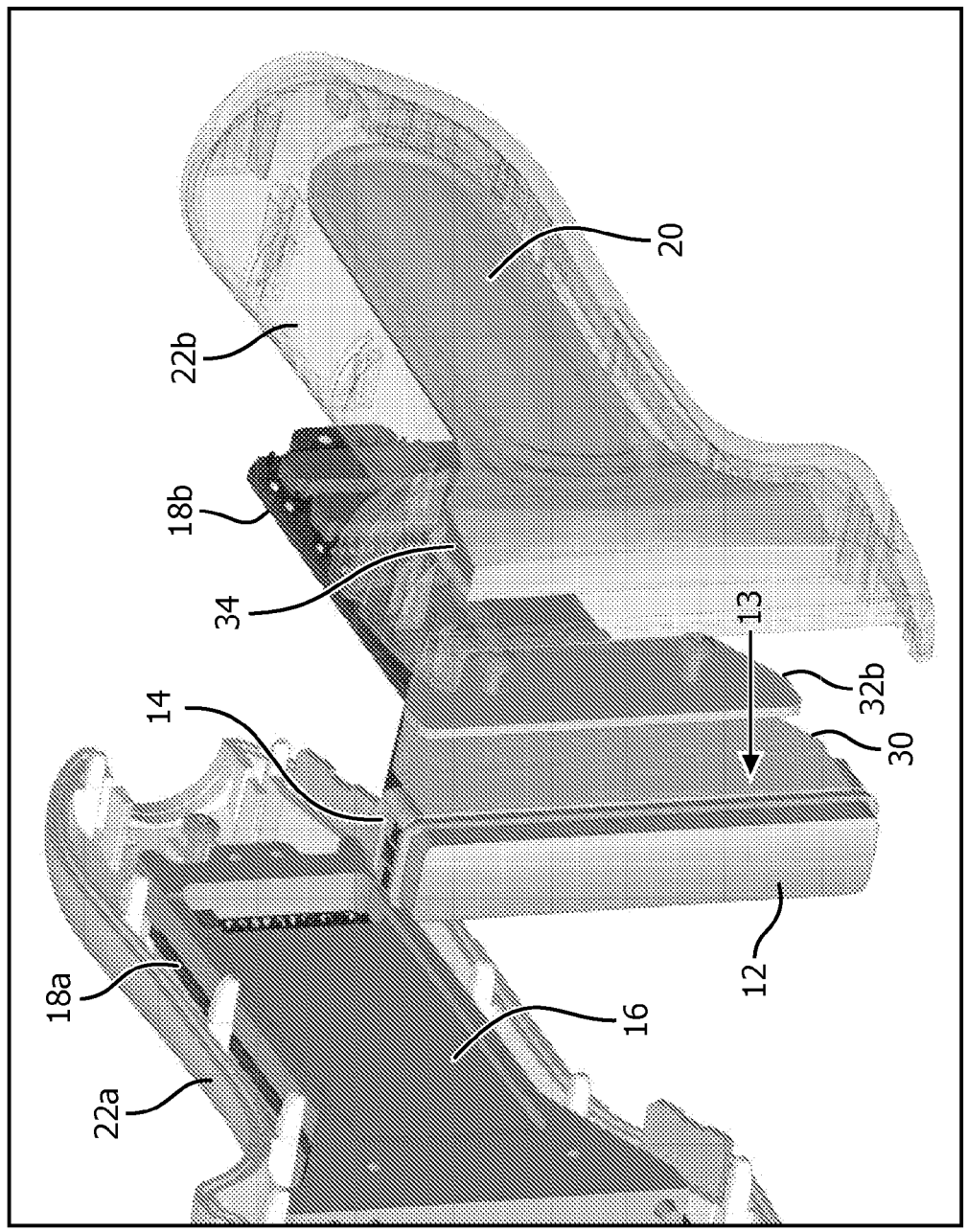
FIG. 2 is a schematic illustration of an additional exploded view of the ultrasound probe shown in FIG. 1 according to an embodiment of the disclosure.

FIG. 2 is a schematic illustration of an additional exploded view of the ultrasound probe 10 according to an embodiment of the disclosure. Certain elements illustrated in FIG. 1 are omitted from FIG. 2 for clarity. Housing portion 22b is shown as translucent FIG. 2 to provide a view of the handle heat spreader 20 on the interior surface of the housing portion 22b. However, it will be appreciated that the housing portions 22a-b may actually be opaque. Although the frame 16 is illustrated to the side of the transducer stack 12 and backing block 14 in FIG. 2, when assembled, the frame 16 may be in line with the transducer stack 12 and backing block 14 as illustrated in FIG. 1. A flexible circuit 30, as mentioned in reference to FIG. 1, may be included in the transducer stack 12. The flexible circuit 30 may be positioned between the transducer stack 12 and the backing block 14. In some embodiments, the flexible circuit 30 may be a layer within the transducer stack 12. The flexible circuit 30 may be able to bend, fold and/or twist. This may allow the flexible circuit 30 to curve around another component and/or conform to a surface. The degree of flexibility of the flexible circuit 30 may be determined, at least in part, by materials chosen for the flexible circuit 30 (e.g., films, conductive elements, circuit components). The flexible circuit 30 may include an insulating polymer film with conductive elements (e.g., wires) applied on one surface. A second insulating polymer film may be applied over the conductive elements and first polymer film. The conductive elements may be made of metals, conductive polymers, or other conductive materials. Some flexible circuits may include multiple alternating layers of elements and insulating film.

The flexible circuit 30 may extend beyond the transducer stack 12 and/or the backing block 14, and be configured to fold down on either long side 13 of the backing block 14 and extend to the printed circuit boards (PCB) 18*a-b*. The flexible circuit 30 may be coupled to the PCBs 18*a-b*. The PCBs 18*a-b* may provide power and control signals to the transducer stack 12 through the flexible circuit 30. The PCBs 18*a-b* may also receive signals from the transducer stack 12 through the flexible circuit 30. In some embodiments, a portion of the flexible circuit 30 may be in contact with and/or coupled to the handle heat spreader 20. Heat from the flexible circuit 30 may be conducted to the handle heat spreader 20, which may dissipate the heat through the housing 22.

In some embodiments, for example the embodiment illustrated in FIG. 2, bolster plates 32*a-b* may be coupled to the top layer of the flexible circuit 30 on each side of the frame 16 (only one bolster plate 32*b* is visible in FIG. 2). The bolster plates 32*a-b* may be secured to the flexible circuit 30 with screws, adhesive, and/or other coupling methods. The bolster plates 32*a-b* may include copper, aluminum, and/or other thermally conducting materials. The bolster plates 32*a-b* may be components of the thermal management system of the probe 10. The bolster plates 32*a-b* may thermally couple one or more thermal management system components on the flexible circuit 30 to the handle heat spreader 20. This may allow heat transferred from the transducer stack 12 to the flexible circuit 30 to be dissipated to the handle of the probe 10. The heat may then dissipate into the air surrounding the probe 10. Heat from the transducer stack 12 may also be transferred to the backing block 14 to the frame 16 as previously described. This may provide three thermal paths rather than a single thermal path to dissipate heat from the transducer stack 12: (1) through the frame 16 and (2-3) the handle heat spreaders 20 on each side of the housing 22*a-b*. As a result, more heat may be dissipated from the transducer stack 12 and/or increase the heat dissipation rate.

In some embodiments, a compressible block 34 may be included in the heat spreader 20 opposite the bolster plate 32*b*. The compressible block 34 may be coupled between the housing 22 and the handle heat spreader 20. In some embodiments, the compressible block 34 may be coupled to a portion of the handle heat spreader 20, and a length of the handle heat spreader 20 may be wrapped around the compressible block 34 as illustrated in FIG. 2. Other configurations may also be possible. The compressible block 34 may urge the handle heat spreader 20 in contact with the bolster plate 32 and/or flexible circuit 30 when the probe 10 is assembled. The compressible block 34 may increase thermal contact between the bolster plate 32*b* and/or flexible circuit 30 and the heat spreader 20. A second compressible block similar to compressible block 34 may be included in the handle heat spreader 20 opposite the bolster plate 32*a* (not shown in FIG. 2). In some embodiments, the compressible block 34 may be implemented with a polymer foam.

In some embodiments, a portion of the handle heat spreader 20 urged against the bolster plates 32*a-b* may be coated with a laminate (not shown) that may reduce thermal resistance. Alternatively, the bolster plates 32*a-b* may be coated with the laminate on a surface adjacent to the handle heat spreader 20. The laminate may improve heat transfer from the bolster plates 32*a-b* to the handle heat spreader 20. An example of a possible laminate is Therm-a-Gap™ G974 available from Parker Chomerics. Other laminates that reduce thermal resistance may also be used.

Figure 3:
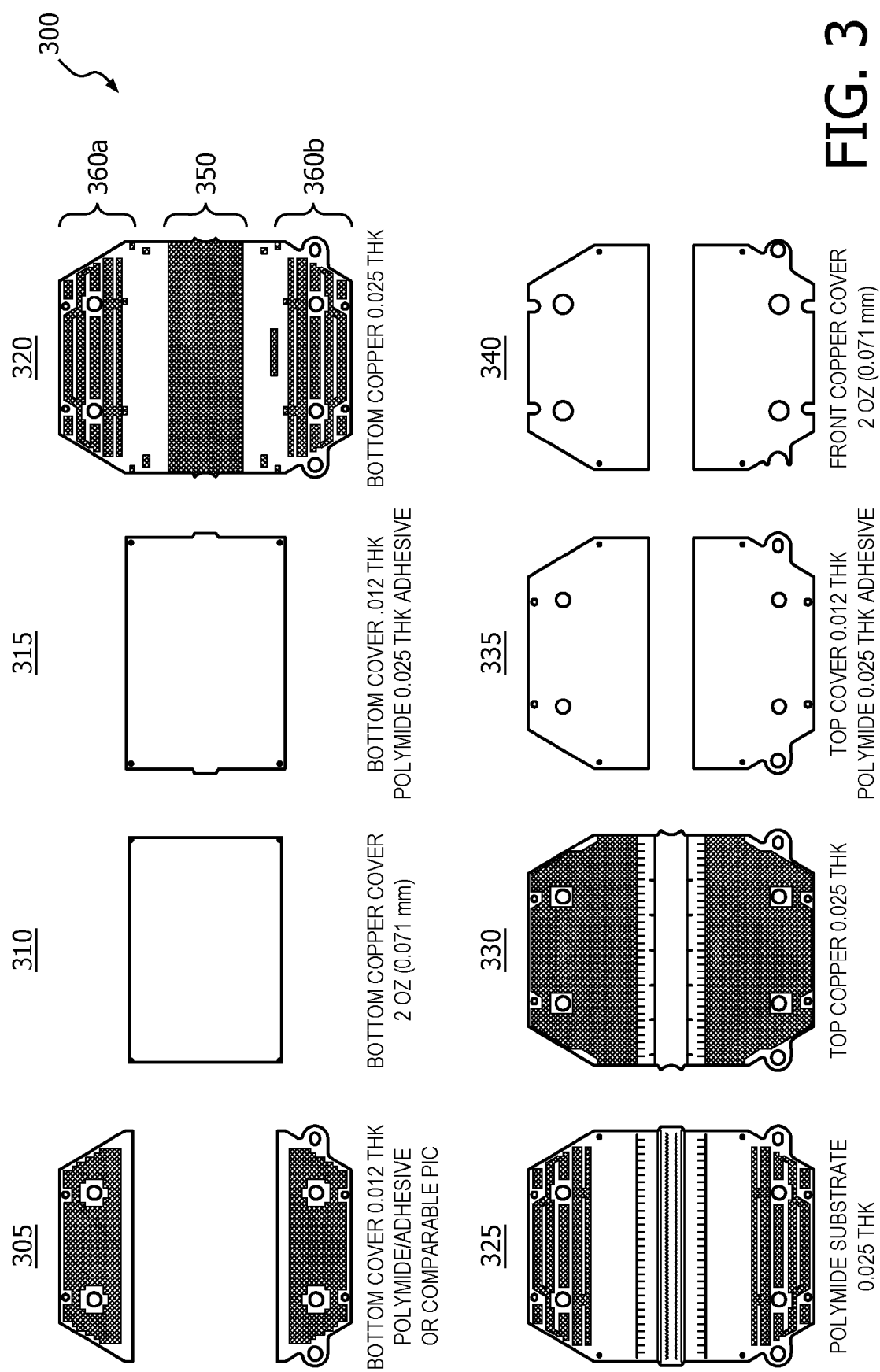
FIG. 3 is a schematic illustration of layers in a flexible circuit including thermal management system components according to an embodiment of the disclosure.

FIG. 3 is a schematic illustration of layers in a flexible circuit 300 including thermal management system components according to an embodiment of the disclosure. The flexible circuit 300 may be used to implement flexible circuit 30 illustrated in FIG. 2 in some embodiments. The flexible circuit 300 may include a central portion 350 that may be placed over the upper surface of a backing block, for example backing block 14 shown in FIG. 2. The flexible circuit 300 may include wing portions 360*a-b* on either side of the central portion 350. The wing portions 360*a-b* may be configured to fold over the edges of the upper surface of the backing block. A first layer may be a non-conductive layer 305. The first non-conductive layer 305 may be included in the wing portions 360*a-b* and coupled to either side of a bottom heat cover 310. The bottom heat cover 310 may be included in the central portion 350. The bottom heat cover 310 may be a component of a thermal management system to dissipate heat from a transducer stack. The bottom heat cover 310 may be covered by a second non-conductive layer 315. A first conductive trace layer 320 may be applied over the second non-conductive layer 315. The first conductive trace layer 320 may provide electrical connections for elements of the transducer stack and/or other electrical components of an ultrasound probe. A non-conductive substrate 325 may be placed over the first conductive trace layer 320. A second conductive trace layer 330 may be applied over the substrate 325. All or portions of the second conductive trace layer 330 may be insulated from the first conductive trace layer 320. A non-conductive top cover 335 may be placed over the second conductive trace layer 330. A top heat cover 340 may be applied over the top cover 335. The top heat cover 340 may cover the wing portions 360*a-b* of flexible circuit 300 that extends from the vertical sides of the backing block. In some embodiments, the wing portions 360*a-b* may extend to one or more printed circuit boards (PCB), for example, PCBs 18*a-b* shown in FIG. 2. In some embodiments, the top heat cover 340 may at least partially cover the central portion 350 flexible circuit 300 that covers the upper surface of the backing block. That is, when a transducer stack is placed on the flexible circuit 300, a portion of the top heat cover 340 may be covered by the transducer stack. The top heat cover 340 may be another component of the thermal management system to dissipate heat from the transducer stack. The top heat cover 340 may be in thermal contact with one or more bolster plates, for example, the bolster plate 32*b* illustrated in FIG. 2. In some embodiments, the top heat cover 340 may be in thermal contact with a handle heat spreader, for example, the handle heat spreader 20 illustrated in FIG. 2. The top heat cover 340 may conduct heat from the flexible circuit 300, including the bottom heat cover 310, to the one or more bolster plates and/or handle heat spreader.

The top and bottom heat covers 340, 310 may be implemented with copper layers in some embodiments. Other thermally conducting materials may be used. The bottom heat cover 310 may reduce thermal resistance between the flexible circuit 300 and the backing block, which may increase heat dissipation from a transducer through the flexible circuit 300 to the backing block. In some embodiments, the bottom heat cover 310 may be omitted. The top heat cover 340 may conduct heat from the transducer stack to the bolster plates and/or the handle heat spreader. The top heat cover 340 may conduct heat from the bottom heat cover 310 and/or the backing block through the flexible circuit 300 to the bolster plates.

Although two conductive trace layers and four non-conductive layers are illustrated in flexible circuit 300, a flexible circuit may have more or fewer conductive trace and/or non-conductive layers. In some embodiments, the conductive trace layers include copper traces. In some embodiments, the non-conductive layers include polyimide and/or polyimide/adhesive composites.

Figure 4:
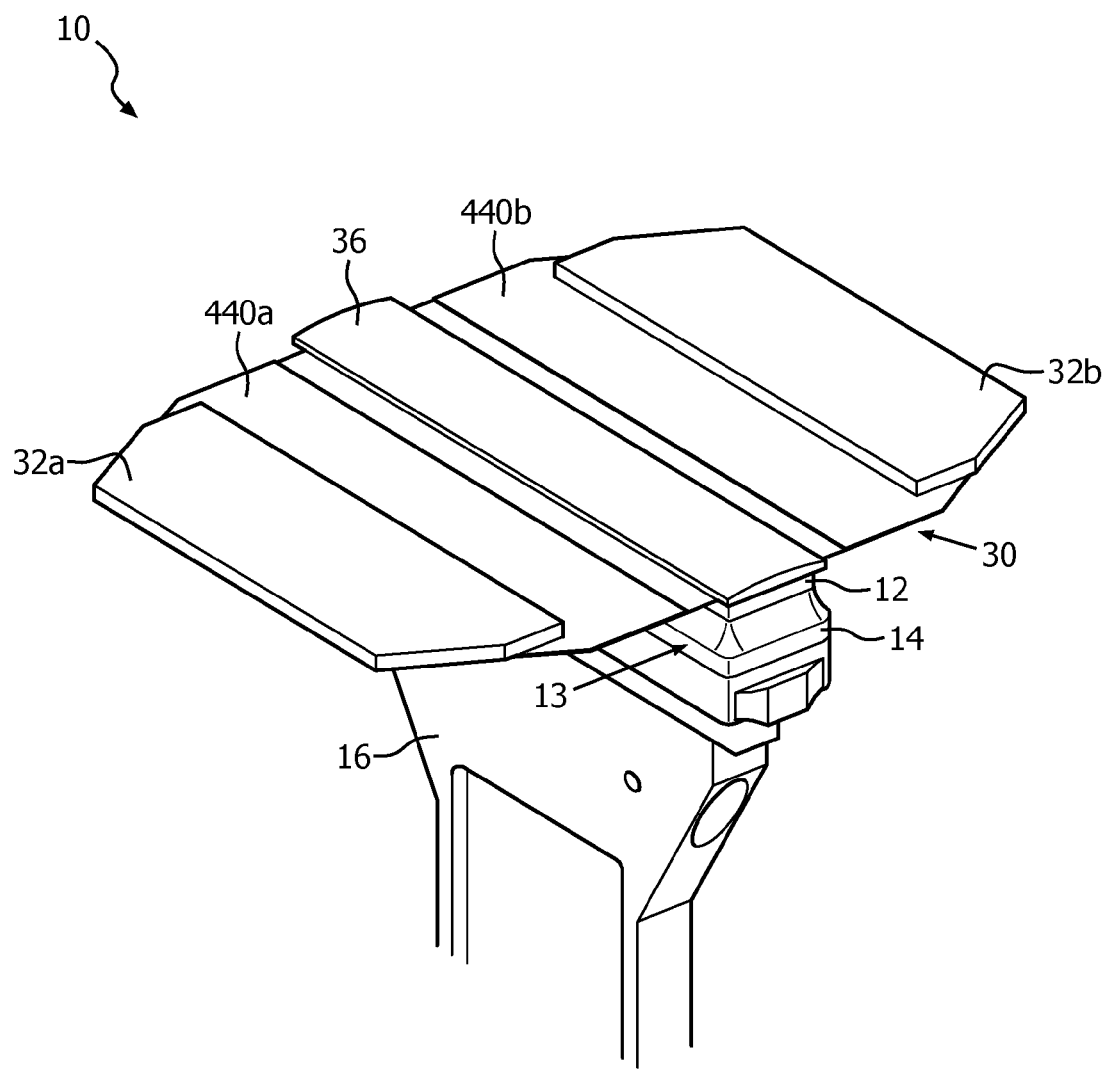
FIG. 4 is a schematic illustration of a portion of the ultrasound probe shown in FIG. 1 according to an embodiment of the disclosure.

FIG. 4 is a schematic illustration of a portion of the ultrasound probe 10 according to an embodiment of the disclosure. The transducer stack 12 with the lens 36 on top is placed on top of the flexible circuit 30 in line with the backing block 14, which is coupled to the frame 16. As shown in FIG. 4, the flexible circuit 30 has not yet been folded down over the sides 13 of the backing block 14. Two portions of a top heat cover 440a-b are located on each end of the flexible circuit 30. The heat cover 440 may be similar to heat cover 340 illustrated in FIG. 3. Two bolster plates 32a-b are each placed on respective portions of the top heat cover 440a-b. However, in some embodiments, the bolster plates 32a-b may not be coupled to the top heat cover 440a-b until after the flexible circuit 30 is folded over the backing block 14 and secured to PCBs (not shown in FIG. 4) on either side of the frame 16. In some embodiments, the bolster plates 32a-b may be omitted.

Figure 5:
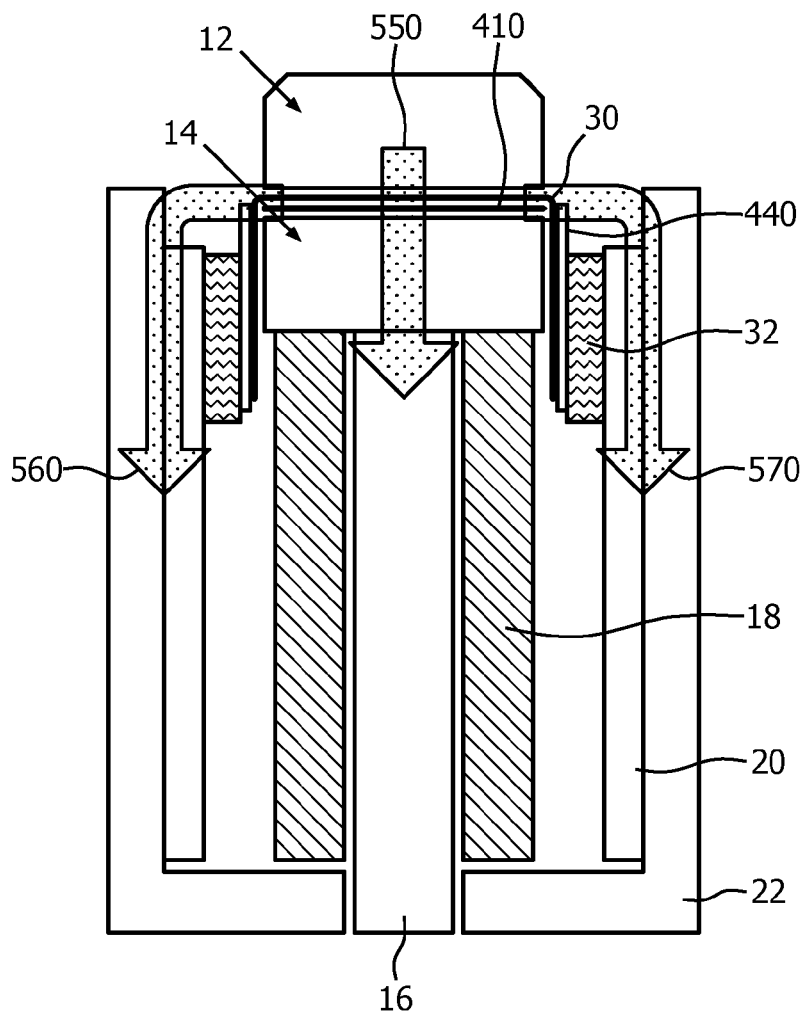
FIG. 5 is a schematic illustration of a side-view of the ultrasound probe shown in FIG. 1 according to an embodiment of the disclosure.

FIG. 5 is a schematic illustration of a side-view of the ultrasound probe 10 according to an embodiment of the disclosure. Three heat paths are indicated by the arrows 550, 560, 570. Heat may be generated by an ultrasound transducer in the transducer stack 12. As indicated by arrow 550, the heat may dissipate through the transducer stack 12 through the flexible circuit 30, through the bottom heat cover 410 of the flexible circuit 30, and into the backing block 14. From the backing block 14, the heat may be conducted into the probe frame 16 through the central portion of the probe 10, as shown by arrow 550. As indicated by arrows 560, 570, heat may dissipate through the transducer stack 12 through the top heat cover 440 of the flexible circuit 30 to bolster plates 32. The heat may be dissipated from the bolster plates 32 into the handle heat spreaders 20, which may dissipate the heat along the probe housing 22 as shown by arrows 560, 570. Although not indicated by an arrow, some heat may be dissipated from the sides of the backing block 14 to the flexible circuit 30, which may dissipate the heat to the bolster plates 32 via the top heat cover 440. As illustrated in FIG. 5, three heat paths may dissipate heat from the transducer stack 12. In some embodiments, only one of the heat paths indicated by arrows 560, 570 may be present. Additional heat paths and/or alternative heat paths to those indicated by arrows 560, 570 may be configured within the probe 10 in some embodiments. For example, additional bolster plates may be coupled to the backing block on sides adjacent to the sides the flexible circuit 30 may cover. The additional bolster plates may couple to additional handle heat spreaders and/or different sections of the handle heat spreaders 20. In another example, the bolster plates 32 may be omitted, and heat may be dissipated through the top heat cover 440 of the flexible circuit 30 to the handle heat spreaders 20.

The thermal management system of the ultrasound probe may be a passive thermal management system. This may reduce cost, size, and weight requirements of the probe compared to an active thermal management system. The thermal management system may include top and bottom heat covers in the flexible circuit, bolster plates coupled to the flexible circuit, and handle heat spreaders located in the ultrasound probe housing in thermal contact within the bolster plates. The thermal management system may improve dissipation of heat from a transducer stack of the probe compared to when only a backing block and probe frame coupled to the backing block are used to dissipate heat from the ultrasound probe. This may allow the transducer stack to use higher energy ultrasound waves, pulses, and/or sequences. The thermal management system may allow the transducer stack to produce higher frequency ultrasound waves, pulses, and/or sequences, which may allow the ultrasound probe to be used for a wider range of imaging and/or therapeutic techniques.

Although the present system has been described with reference to an ultrasound imaging system, the present system may be extended to other ultrasound transducers. Additionally, the present system may be used to obtain and/or record image information related to, but not limited to renal, testicular, prostate, breast, ovarian, uterine, thyroid, hepatic, lung, musculoskeletal, splenic, nervous, cardiac, arterial and vascular systems, as well as other imaging applications related to ultrasound-guided interventions and other interventions which may be guided by real-time medical imaging. Further, the present system may also include one or more elements which may be used with non-ultrasound imaging systems with or without real-time imaging components so that they may provide features and advantages of the present system.

Further, the present methods, systems, and apparatuses may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging.

Certain additional advantages and features of this invention may be apparent to those skilled in the art upon studying the disclosure, or may be experienced by persons employing the novel system and method of the present invention, chief of which is thermal dissipation in ultrasound transducers and method of operation thereof is provided. Another advantage of the present systems and method is that conventional medical image systems may be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:
1. An ultrasound probe, comprising:
   a transducer stack;
   a backing block including a first surface, a second surface opposite the first surface, and a side extending between the first and second surfaces;

a flexible circuit including:
- a flexible non-conductive substrate including:
  - a central portion disposed between the transducer stack and the backing block; and
  - a wing portion coupled to the central portion, the wing portion configured to fold adjacent to the side of the backing block;
- a first heat cover disposed below the central portion and adjacent to the first surface of the backing block wherein the first heat cover is configured to dissipate heat from the transducer stack; and
- a second heat cover disposed over the wing portion, wherein the second heat cover is configured to dissipate heat from the transducer stack;

a bolster plate in thermal contact with the second heat cover; and a handle heat spreader in thermal contact with the bolster plate, wherein the handle heat spreader is configured to dissipate heat from the bolster plate.

2. The ultrasound probe of claim 1, further comprising a probe housing configured to at least partially enclose the transducer stack, backing block, flexible circuit, bolster plate, and handle heat spreader.

3. The ultrasound probe of claim 2, wherein the handle heat spreader is coupled to an interior surface of the probe housing.

4. The ultrasound probe of claim 3, further comprising a compressible block disposed between a portion of the handle heat spreader and the interior surface of the probe housing, wherein the compressible block is configured to urge the handle heat spreader against the bolster plate.

5. The ultrasound probe of claim 1, further comprising a laminate disposed between the bolster plate and the handle heat spreader, wherein the laminate is configured to reduce thermal resistance between the bolster plate and the handle heat spreader.

6. The ultrasound probe of claim 1, wherein the first and second heat covers comprise copper.

7. The ultrasound probe of claim 1, further comprising a probe frame coupled to the second surface of the backing block.

8. The ultrasound probe of claim 7, further comprising a printed circuit board coupled to the probe frame and the flexible circuit.

9. The ultrasound probe of claim 1, wherein the handle heat spreader comprises copper.

10. The ultrasound probe of claim 1, wherein the flexible circuit further comprises:
- a first non-conductive layer on the wing portion, the first non-conductive layer coupled to two parallel sides of the first heat cover;
- a second non-conductive layer over the first heat cover;
- a first conductive trace layer over the first and second non-conductive layers wherein the flexible non-conductive substrate is over the first conductive trace layer;
- a second conductive trace layer over the first non-conductive layer; and
- a non-conductive top cover over the second conductive trace layer on the wing portion.

11. The ultrasound probe of claim 10, wherein the first and second heat covers of the flexible circuit comprise copper.

12. The ultrasound probe of claim 10, wherein the first and second conductive trace layers of the flexible circuit comprise copper.

13. The ultrasound probe of claim 10, wherein the first and second conductive trace layers of the flexible circuit are at least partially electrically insulated from each other.

14. The ultrasound probe of claim 10, wherein the first and second non-conductive layers, the flexible non-conductive substrate, and the non-conductive top cover of the flexible circuit comprise polyimide.

15. The ultrasound probe of claim 1, wherein the backing block comprises graphite.

* * * * *